(12) United States Patent
Mohana Rangan et al.

(10) Patent No.: US 12,085,544 B2
(45) Date of Patent: Sep. 10, 2024

(54) METHODS FOR SIMULTANEOUS QUANTIFICATION OF ANIONS USING ION CHROMATOGRAPHY AND SUPPRESSED ION CONDUCTIVITY

(71) Applicants: Srivatsan Mohana Rangan, Tempe, AZ (US); Anca Delgado, Tempe, AZ (US); Rosa Krajmalnik-Brown, Chandler, AZ (US)

(72) Inventors: Srivatsan Mohana Rangan, Tempe, AZ (US); Anca Delgado, Tempe, AZ (US); Rosa Krajmalnik-Brown, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 421 days.

(21) Appl. No.: 17/498,203

(22) Filed: Oct. 11, 2021

(65) Prior Publication Data
US 2022/0113287 A1 Apr. 14, 2022

Related U.S. Application Data

(60) Provisional application No. 63/089,945, filed on Oct. 9, 2020.

(51) Int. Cl.
*G01N 30/54* (2006.01)
*G01N 30/64* (2006.01)
(Continued)

(52) U.S. Cl.
CPC .............. *G01N 30/54* (2013.01); *G01N 30/64* (2013.01); *G01N 30/8679* (2013.01); *G01N 33/182* (2013.01)

(58) Field of Classification Search
None
See application file for complete search history.

(56) References Cited

U.S. PATENT DOCUMENTS 4,925,567 A * 5/1990 McAleese .............. G01N 30/96
210/659
5,132,018 A * 7/1992 Jones ..................... G01N 30/96
210/656
(Continued)

FOREIGN PATENT DOCUMENTS

| CN | 106645460 A | * | 5/2017 | ............. G01N 30/02 |
| CN | 106568886 B | * | 11/2018 | ............. G01N 30/96 |
| CN | 110412195 A | * | 11/2019 | ............. G01N 30/88 |

OTHER PUBLICATIONS

Li, Zong-li et al., Sequential Determination of Arsenite and Arsenate by Ion Chromatography, Analytica Chimica Acta, vol. 307, 1995, pp. 79-87.*

(Continued)

*Primary Examiner* — Daniel S Larkin
(74) *Attorney, Agent, or Firm* — Quarles & Brady, LLP

(57) ABSTRACT

Methods and systems for the detection and quantification of multiplicity of ionic analytes comprising $CrO_4^{2-}$, $AsO_4^{3-}$, $SeO_4^{2-}$, and $ClO_4^-$, and optionally $F^-$, $Cl^-$, $NO_2^-$, $NO_3^-$, $SO_4^{2-}$, using ion chromatography and suppressed ion conductivity. The method comprises loading a sample loop with a sample; injecting the sample from the sample loop into a column with an eluent, wherein the column comprises a guard column and an analytical column; separating, with the column, the injected sample at an effective separation temperature the injected sample in the presence of an organic modifier into a multiplicity of detectable ionic analytes; suppressing, with a suppressor, background signal; and detecting, with a detector, the multiplicity of ionic analytes.

18 Claims, 4 Drawing Sheets

(51) Int. Cl.
*G01N 30/86* (2006.01)
*G01N 33/18* (2006.01)

(56) References Cited

U.S. PATENT DOCUMENTS

| | | | | |
|---|---|---|---|---|
| 6,153,101 | A * | 11/2000 | Schafer | G01N 30/96 210/659 |
| 2007/0065343 | A1* | 3/2007 | Srinivasan | G01N 30/463 422/70 |

OTHER PUBLICATIONS

Karmarkar, S.V et al., "Determination of Oxyanions in Solutions Equilibrated with Soils", Chromatographia, vol. 34, No. 11/12, Dec. 1992, pp. 643-647.*
Marques, M.N. et al., "Determination of Glyphosate in Water Samples by IC", Journal of Chromatographic Studies, vol. 47, Oct. 2009, pp. 822-824.*
Jackson, P.E. et al., "Determination of Trace Level Perchlorate in Drinking Water and Ground Water by Ion Chromatography", Journal of Chromatography A, vol. 850, 1999, pp. 131-135.*
Michalski, R. et al., "Matrix Influences on the Determination of Common Ions by Using Ion Chromatography Part 1—Determination of Inorganic Anions", Journal of Chromatographic Science, vol. 50, 2012, pp. 482-493.*
"Suppression in Ion Chromatography", Metrohm, Apr. 2014, pp. 1-8.*
Bhandari, N., Reeder, R.J., Strongin, D.R., 2011. Photoinduced oxidation of arsenite to arsenate on ferrihydrite. Environmental science & technology 45, 2783-2789.
Bruzzoniti, M.C., Mentasti, E., Sarzanini, C., 1999. "Simultaneous determination of inorganic anions and metal ions by suppressed ion chromatography," Analytica chimica acta 382, 291-299.
California Water boards, 2018. Hexavalent Chromium in Drinking Water.
Delgado, A.G., Parameswaran, P., Fajardo-Williams, D., Halden, R.U., Krajmalnik-Brown, R., 2012. Role of bicarbonate as a pH buffer and electron sink in microbial dechlorination of chloroethenes. Microbial cell factories 11, 128.
Destanoğlu, O., Gümüş Yilmaz, G., 2016. "Determination of cyanide, thiocyanate, cyanate, hexavalent chromium, and metal cyanide complexes in various mixtures by ion chromatography with conductivity detection." Journal of Liquid Chromatography & Related Technologies 39, 465-474.
El-Shahawi, M., Bashammakh, A., Abdelmageed, M., 2011. Chemical speciation of chromium (III) and (VI) using phosphonium cation impregnated polyurethane foams prior to their spectrometric determination. Analytical Sciences 27, 757-763.
Gammelgaard, B., Liao, Y.-p., Jøns, O., 1997. "Improvement on simultaneous determination of chromium species in aqueous solution by ion chromatography and chemiluminescence detection." Analytica chimica acta 354, 107-113.
Gandhi, S., Oh, B.-T., Schnoor, J.L., Alvarez, P.J., 2002. Degradation of TCE, Cr (VI), sulfate, and nitrate mixtures by granular iron in flow through columns under different microbial conditions. Water Research 36, 1973-1982.
Hautman, D.P., Munch, D.J., Eaton Andrew, D., Haghani Ali, W., 1999. EPA Method 314.0: Determination of perchlorate in drinking water using ion chromatography.
Joe-Wong, C., Brown Jr, G.E., Maher, K., 2017. Kinetics and products of chromium (VI) reduction by iron (II/III)-bearing clay minerals. Environmental science & technology 51, 9817-9825.
Karlson, U., Frankenberger Jr, W., 1986. Determination of selenate by single-column ion chromatography. Journal of Chromatography A 368, 153-161.
Khamkhash, A., Srivastava, V., Ghosh, T., Akdogan, G., Ganguli, R., Aggarwal, S., 2017. Mining-related selenium contamination in Alaska, and the state of current knowledge. Minerals 7, 46.
Kim, C., Zhou, Q., Deng, B., Thornton, E.C., Xu, H., 2001. Chromium (VI) reduction by hydrogen sulfide in aqueous media: stoichiometry and kinetics. Environmental science & technology 35, 2219-2225.
Kończyk, J., Muntean, E., Michalski, R., 2018. Simultaneous determination of chromate and common inorganic anions using suppressed ion chromatography. Chemistry, Environment, Biotechnology 21, 11-13.
Lee, H., Choi, W., 2002. Photocatalytic oxidation of arsenite in $TiO_2$ suspension: kinetics and mechanisms. Environmental science & technology 36, 3872-3878.
Löffler, F.E., Sanford, R.A., Ritalahti, K.M., 2005. Enrichment, cultivation, and detection of reductively dechlorinating bacteria. Methods in enzymology 397, 77-111.
Metrohm USA, Determination of Hexavalent Chromium (Cr+6) by US EPA Method 218.7 (2011).
Miao, Z., Brusseau, M.L., Carroll, K.C., Carreón-Diazconti, C., Johnson, B., 2012. Sulfate reduction in groundwater: characterization and applications for remediation. Environmental geochemistry and health 34, 539-550.
Michalski, R., Ion chromatography method for the determination of trace levels of chromium (VI) in water. Polish Journal of Environmental Studies 2004, 13(1):73-77.
Mohana Rangan et al., "An ion chromatography method for simultaneous quantification of chromate, arsenate, selenate, perchlorate, and other inorganic anions in environmental media," Manuscript Chromate IC method Srivats, 2021, 38(7): 626-634.
Munch, D.J., Wasko, M., Flynt, E., Wendelken, S.C., Scifres, J., Mario, J.R., Hunt, M., Gregg, D., Schaeffer, T., Clarage, M., 2005. Validation and Peer Review of US Environmental Protection Agency Chemical Methods of Analysis.
Onchoke, K.K., Sasu, S.A., 2016. Determination of Hexavalent Chromium (Cr (VI)) concentrations via ion chromatography and UV-Vis spectrophotometry in samples collected from nacogdoches wastewater treatment plant, East Texas (USA). Advances in Environmental Chemistry 2016.
Parker, D.R., Seyfferth, A.L., Reese, B.K., 2008. Perchlorate in groundwater: a synoptic survey of "pristine" sites in the coterminous United States. Environmental science & technology 42, 1465-1471.
Pyrzyńska, K., 2002. Determination of selenium species in environmental samples. Microchimica Acta 140, 55-62.
Salnikow, K., Zhitkovich, A., 2008. Genetic and epigenetic mechanisms in metal carcinogenesis and cocarcinogenesis: nickel, arsenic, and chromium. Chemical research in toxicology 21, 28-44.
Shrivastava, A., Gupta, V.B., 2011. Methods for the determination of limit of detection and limit of quantitation of the analytical methods. Chronicles of young scientists 2, 21.
Šikovec, M., Franko, M., Novič, M., Veber, M., 2001. Effect of organic solvents in the online thermal lens spectrometric detection of chromium (III) and chromium (VI) after ion chromatographic separation. Journal of Chromatography A 920, 119-125.
Steinmaus, C.M., 2016. Perchlorate in water supplies: sources, exposures, and health effects. Current environmental health reports 3, 136-143.
Thermo Fisher Scientific, Sensitive Determination of Hexavalent Chromium in Drinking Water. Thermo Scientific, 2013. Dionex onguard II cartridges. Prod Man P, 25.
Urbansky, E.T., 2002. Perchlorate as an environmental contaminant. Environmental Science and Pollution Research 9, 187-192.
US EPA, 1992. Method 7196A: Chromium, Hexavalent (Colorimetric).
US EPA, 2007. Method 9056A: Determination of inorganic anions by ion chromatography.
US EPA, 2010. Chromium in Drinking Water.
Wang, Z., Bush, R.T., Sullivan, L.A., Liu, J., 2013. Simultaneous redox conversion of chromium (VI) and arsenic (III) under acidic conditions. Environmental science & technology 47, 6486-6492.
World Health Organization, 2003. Guidelines for Drinking-water Quality | Chromium.
World Health Organization, 2020. Arsenic—Fact sheets.

(56) References Cited

OTHER PUBLICATIONS

Yeo, J., Choi, W., 2009. Iodide-mediated photooxidation of arsenite under 254 nm irradiation. Environmental science & technology 43, 3784-3788.

Yoon, J., Amy, G., Chung, J., Sohn, J., Yoon, Y., 2009. Removal of toxic ions (chromate, arsenate, and perchlorate) using reverse osmosis, nanofiltration, and ultrafiltration membranes. Chemosphere 77, 228-235.

Zaffiro, A., Zimmerman, M., Wendelken, S., Smith, G., Munch, D., 2011. Method 15 218.7: Determination of hexavalent chromium in drinking water by ion chromatography with postcolumn derivatization and UV-Visible spectroscopic detection.

Zhitkovich, A., 2011. Chromium in drinking water: sources, metabolism, and cancer risks. Chemical research in toxicology 24, 1617-1629.

Ziv-El, M., Delgado, A.G., Yao, Y., Kang, D.-W., Nelson, K.G., Halden, R.U., Krajmalnik-Brown, R., 2011. Development and characterization of DehaloR2, a novel anaerobic microbial consortium performing rapid dechlorination of TCE to ethene. Applied microbiology and biotechnology 92, 1063-1071.

Rakhunde, R., Deshpande, L., Juneja, H., 2012. Chemical speciation of chromium in water: a review. Critical reviews in environmental science and technology 42, 776-810.

Costa, M., 1997. Toxicity and carcinogenicity of Cr (VI) in animal models and humans. Critical reviews in toxicology 27, 431-442.

Jin M. Chen & Oliver J. Hao (1998): Microbial Chromium (VI) Reduction, Critical Reviews in Environmental Science and Technology, 28:3, 219-251.

Mehra, H., Frankenberger, W., 1988. Simultaneous analysis of selenate and selenite by single-column ion chromatography. Chromatographia 25, 585-588.

Ike, M., Miyazaki, T., Yamamoto, N., Sei, K., Soda, S., 2008. Removal of arsenic from groundwater by arsenite-oxidizing bacteria. Water Science and Technology 58, 1095-1100.

Cohen, M.D., Kargacin, B., Klein, C.B., Costa, M., 1993. Mechanisms of chromium carcinogenicity and toxicity. Critical reviews in toxicology 23, 255-281.

\* cited by examiner

Figure 4
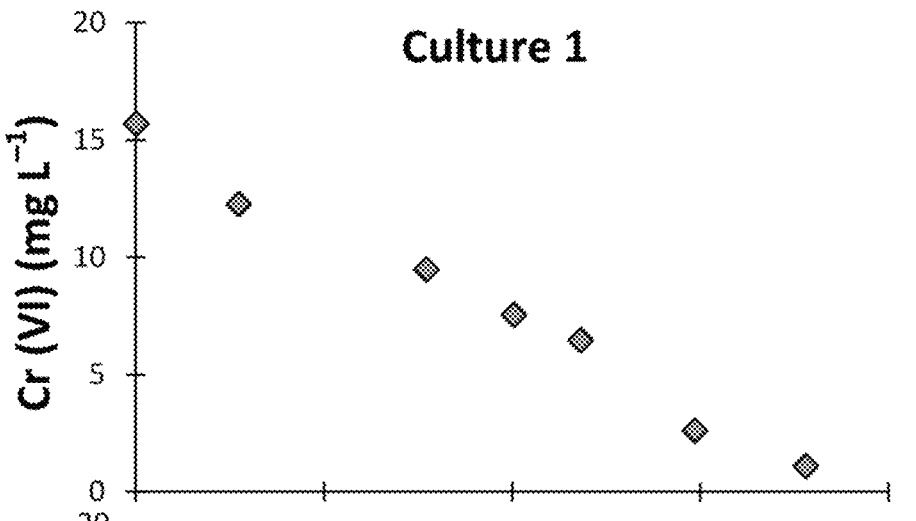
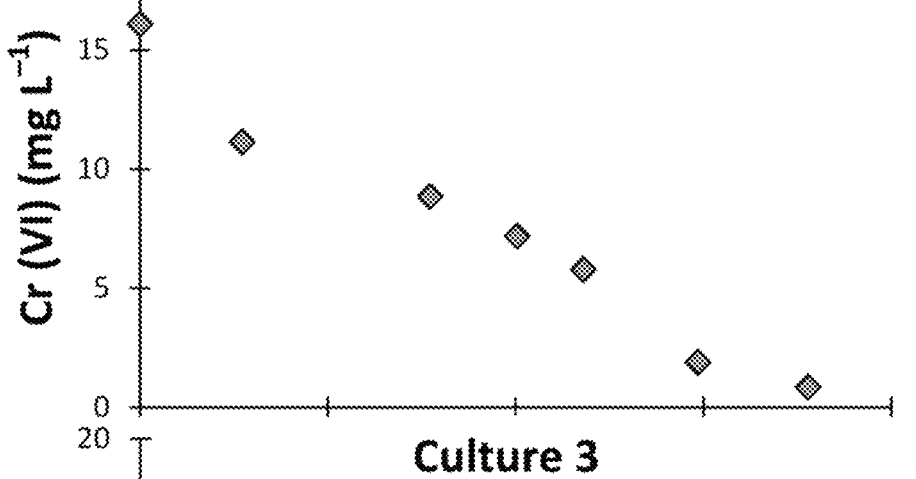
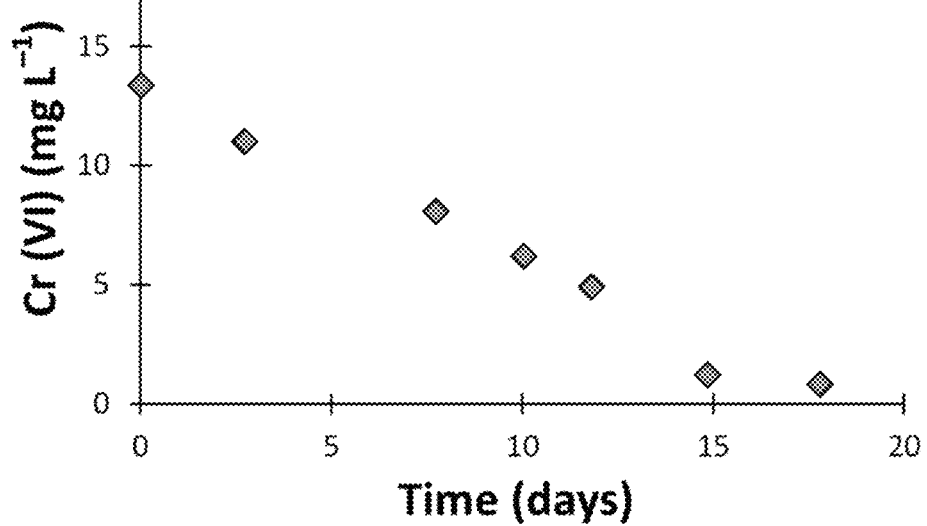

METHODS FOR SIMULTANEOUS QUANTIFICATION OF ANIONS USING ION CHROMATOGRAPHY AND SUPPRESSED ION CONDUCTIVITY

CROSS-REFERENCE TO RELATED APPLICATIONS

This application claims benefit of priority to U.S. Patent Application Ser. No. 63/089,945, filed Oct. 9, 2020, the contents of which is incorporated by reference in its entirety.

STATEMENT REGARDING FEDERALLY SPONSORED RESEARCH

This invention was made with government support under 1449501 awarded by the National Science Foundation. The government has certain rights in the invention.

FIELD OF THE INVENTION

The disclosed technology is generally directed to ion chromatography. More particularly the technology is directed to simultaneous quantification of chromate, arsenate, selenate, perchlorate, and other inorganic anions.

BACKGROUND OF THE INVENTION

Chromium (VI) is a toxic, mutagenic, and carcinogenic water pollutant. The World Health Organization set a maximum allowable limit of 50 µg $L^1$ for Cr (VI) in groundwater and drinking water (World Health Organization, 2003). In the United States, the drinking water maximum contaminant level (MCL) set by the Environmental Protection Agency (EPA) is 100 µg $L^{-1}$ total Cr (US EPA, 2010). At the state level, the MCL can be even lower (e.g., 50 µg $L^{-1}$ as total Cr in California) (California Water boards, 2018). The standard ion chromatography (IC) method for quantification of chromate ($CrO_4^{2-}$), the most common Cr (VI) anion, in water samples is EPA Method 218.7 (Zaffiro et al., 2011). Method 218.7 involves the separation of $CrO_4^{2-}$ using a high-capacity anion exchange separator column, a post-column derivatization with Cr (VI)-specific reagent 1,5-diphenylcarbazide, and a UV-Vis detection of the colored complex at 530 nm. The Cr (VI)-specific reagent diphenylcarbazide and UV-Vis detection allow sensitive quantification of Cr (VI) at low µg $L^{-1}$ concentrations by avoiding interference from other anions like sulfate ($SO_4^{2-}$). However, method 218.7 and methods using similar principles are Cr (VI)-specific and do not quantify other analytes present in a given sample.

Cr (VI) often co-occurs with one or more common inorganic anions, such as $Cl^-$, $SO_4^{2-}$, and $NO_3^-$, in drinking water, industrial wastewater, surface waters, groundwater, acid mine drainage, soils, and sediments. In groundwater, acid mine drainage and other process waters, Cr (VI) is often a co-contaminant with other regulated anions such as arsenate ($AsO_4^{3-}$) and selenate ($SeO_4^{2-}$) (As (V) and Se (VI) anions, respectively) and/or perchlorate ($ClO_4^-$). $ClO_4^-$ and Cr (VI) are frequently co-detected in drinking water systems across the world. Most laboratories use IC with conductivity detection to simultaneously quantify $Cl^-$, $SO_4^{2-}$ and $NO_3^-$ using EPA Method 9056A (US EPA, 2007). Separate IC methods with conductivity detection have been reported for quantification of $ClO_4^-$ (EPA Method 314.0), As (V), and (Se (VI)). Thus, analysis of surface water, groundwater, acid mine drainage, and other environmental aqueous samples containing Cr (VI) and co-occurring anions requires multiple IC analytical methods with different anion exchange columns and eluent composition. This requirement not only increases the sample volume demand but also the time and overall cost of analysis.

A limited numbers of studies achieved separation and detection of Cr (VI), As (V) and Se (VI) in the presence of common inorganic anions using anion exchange columns and conductivity detection (Bruzzoniti et al., 1999; Kończyk et al., 2018). However, linearity, precision, and accuracy of the co-detected analytes were not evaluated in these studies, limiting the methods' applicability to environmental samples commonly analyzed in academic or other research-focused laboratories.

BRIEF SUMMARY OF THE INVENTION

Disclosed herein is an isocratic ion chromatography (IC) analytical method with suppressed conductivity detection for simultaneous quantification of chromium (VI) and other relevant ions. The method comprises loading a sample loop with an aqueous sample, injecting the sample from the sample loop into a column with an eluent, wherein the column comprises a guard column and an analytical column, separating, with the column, the injected sample at an effective separation temperature in the presence of an organic modifier into a multiplicity of detectable ionic analytes comprising Cr (VI), Se (VI), As (V), and $ClO_4^-$, suppressing, with a suppressor, background signal, and detecting, with a detector, the multiplicity of ionic analytes comprising Another aspect of the invention comprises a system for simultaneous quantification of anions. The system comprises an eluent, an organic modifier, an injector, a column, the column comprising a guard column and an analytical column, a suppressor, and a detector, wherein the system is configured for detection of a multiplicity of ionic analytes comprising Cr (VI), Se (VI), As (V), and $ClO_4^-$.

In some embodiments, the method and system are configured for simultaneous detection of $CrO_4^{2-}$, $F^-$, Cl, $NO_2^-$, $NO_3^-$, $SO_4^{2-}$, $AsO_4^{3-}$, $SeO_4^{2-}$, and $ClO_4^-$.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 4 shows the concentrations of Cr (VI) during incubation in replicate culture-only microcosms.

DETAILED DESCRIPTION OF THE INVENTION

Figure 1:
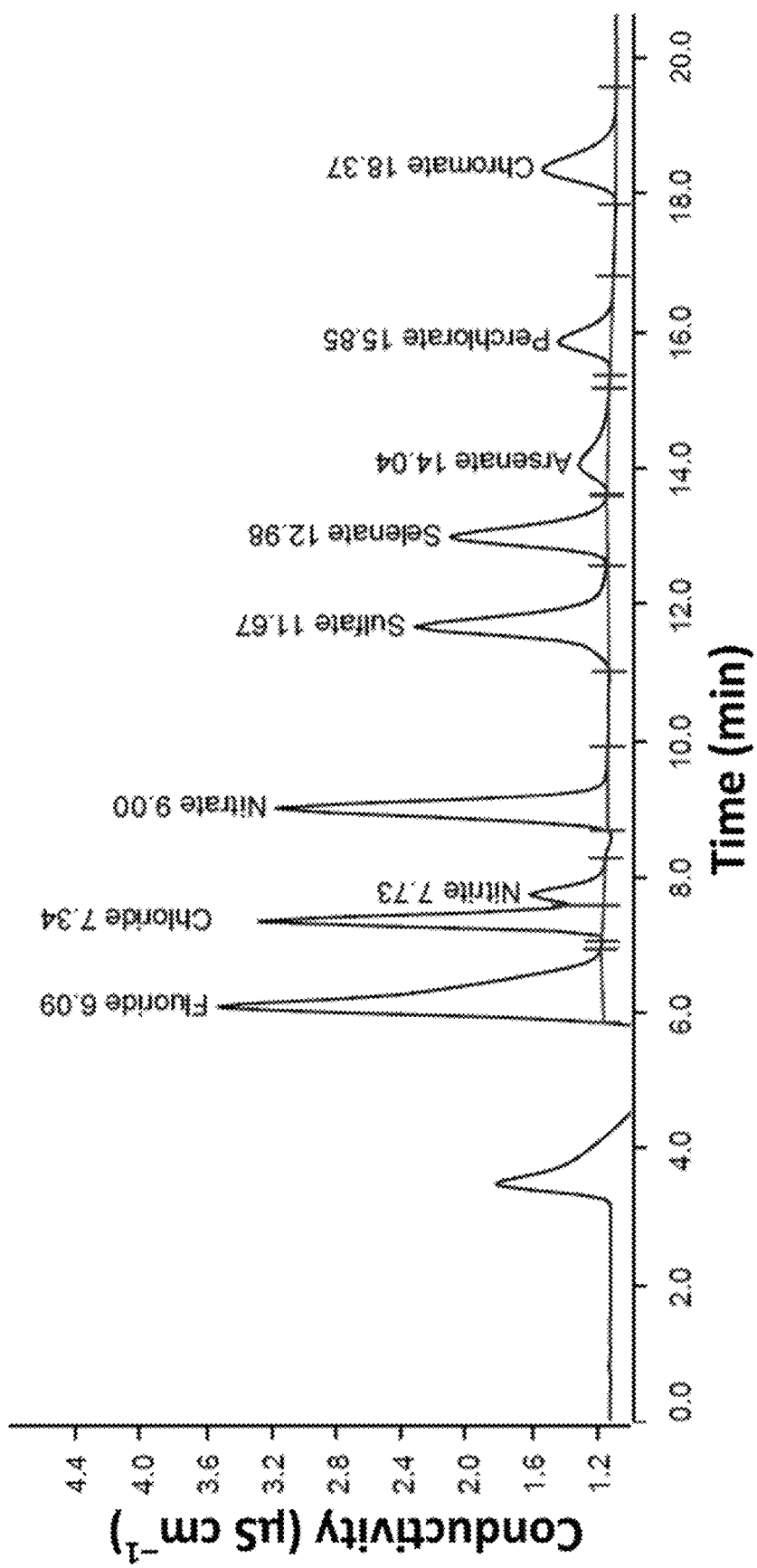
FIG. 1 shows an IC chromatogram of a mixture of 50 µg $L^{-1}$ each of Cr (VI), $ClO_4^-$, $SO_4^{2-}$ and other anions with a Metrohm Metrosep A Supp 7 analytical column and mobile phase containing 10.8 mM $Na_2CO_3$ eluent and 35% (v/v) acetonitrile.

Disclosed herein is an isocratic ion chromatography (IC) analytical method with suppressed conductivity detection for simultaneous quantification of chromium (VI), a toxic, mutagenic, and carcinogenic water pollutant, and other environmentally-relevant anions: $F^-$, $Cl^-$, $NO_2^-$, $NO_3^-$, $SO_4^{2-}$, Se (VI), As (V), and $ClO_4^-$. The method was validated by determining the linearity and accuracy (precision and trueness) for all the anion analytes. The method was used to evaluate recovery of Cr (VI) in tap water, surface water, groundwater and industrial wastewater samples and to analyze Cr (VI), $SO_4^{2-}$, $NO_3^-$, and $Cl^-$ in laboratory samples.

The present technology allows for Cr (VI), As (V), Se (VI) and $ClO_4^-$ to be measured in a low $\mu g\ L^{-1}$ concentration range without pre-treatment of the sample or post column derivatization. The ability to measure ionic analytes may be characterized by one or more of the following relationships. Resolution of two peaks (R), defined as the ratio of the difference in retention times between two peaks and the average baseline width of two peaks, may be determined using Equation 1:

$$R = \frac{T_{R2} - T_{R1}}{(w_{b1} + w_{b2})/2} \quad \text{(Equation 1)}$$

where $T_{R1}$ and $T_{R2}$ are the retention times of adjacent peaks (analyte 1 elutes before analyte 2) and $w_{b1}$ and $w_{b2}$ are the widths of the peaks at baseline. The limit of detection (LOD), defined as the smallest concentration of analyte in a sample that can be readily distinguished from zero, may be determined using Equation 2:

$$LOD = \frac{3S_a}{b} \quad \text{(Equation 2)}$$

The limit of quantification (LOQ), defined as the smallest concentration of analyte in a sample that can be quantitatively determined with suitable precision and accuracy, may be determined using Equation 3:

$$LOQ = \frac{10S_a}{b} \quad \text{(Equation 3)}$$

In Equations 2 and 3, $S_a$ is the standard deviation of the response estimated by the standard error of y-intercepts of the regression lines and b is the slope of the calibration curve (Shrivastava and Gupta, 2011). Accuracy, defined as the closeness between a measured value and either a true or accepted value, was evaluated by determining the precision and trueness of each analyte (Munch et al., 2005). The precision and trueness may be determined by calculating the relative standard deviation (RSD) and the recovery using Equations 4 and 5, respectively:

$$RSD\ (\%) = \frac{\text{Standard deviation of measured concentrations}}{\text{Average of measured concentrations } (\mu g\ L^{-1})} \times 100 \quad \text{(Equation 4)}$$

$$Recovery\ (\%) = \frac{\text{Average of measured concentrations } (\mu g\ L^{-1})}{\text{Spiked concentration } (\mu g\ L^{-1})} \times 100 \quad \text{(Equation 5)}$$

As used herein, a "low $\mu g\ L^{-1}$ concentration range" refers to a LOD less than 10.0 $\mu g\ L^{-1}$ and LOQ less than 30.0 $\mu g\ L^{-1}$. In some embodiments, the LOD is less than 8.0, 6.0, 4.0, 2.0, 1.8, 1.6, 1.4, 1.2, 1.0, 0.8, 0.6, 0.4, or 0.2 depending on the analyte of interest. In some embodiments, the LOD is less than 25.0, 20.0, 15.0, 10.0, 5.0, 4.0, 3.0, 2.0, 1.8, 1.6, 1.4, 1.2, 1.0, 0.8, or 0.6 depending on the analyte of interest.

The standard IC method for quantification of Cr (VI) in water samples is EPA Method 218.7, which requires post column derivatization with 1,5-diphenylcarbazide and UV-Vis spectroscopy detection. Method 218.7 is Cr (VI)-specific; thus, it does not allow detection of co-occurring natural and anthropogenic anions in environmental media.

In contrast to the EPA methodology, an isocratic IC method with suppressed conductivity detection is disclosed. As demonstrated in the Examples that follow, the method utilizing a Metrohm Metrosep A Supp 7 column, and sodium carbonate/acetonitrile as a mobile phase for simultaneous quantification of Cr (VI) as chromate ion, $ClO_4^-$, As (V) as arsenate ion, Se (VI) as selenate ion. Each of these analytes may be detected in a low $\mu g\ L^{-1}$ concentration range. The method also advantageously allows for simultaneous quantification of common anions $F^-$, $Cl^-$, $NO_2^-$, $NO_3^-$, and $SO_4^{2-}$ with Cr (VI), $ClO_4^-$, As (V), and Se (VI) in a low $\mu g\ L^{-1}$ concentration range. "Simultaneous" means that the presence or concentration of two or more analytes may be qualitatively or quantitatively determined with a single analytical method using the same column and eluent in a single run.

The determination coefficient for every analyte was >0.99 and the method showed good accuracy (precision and trueness) in quantification of each analyte. For Cr (VI), the LOD and the LOQ were 0.2 $\mu g\ L^{-1}$ and 0.6 $\mu g\ L^{-1}$, respectively, which are three orders of magnitude lower than the EPA drinking water maximum contaminant level of 100 $\mu g\ L^{-1}$ Cr. Cr (VI) recovery in environmental aqueous samples ranged from 97.2% to 102.8%. The method was successfully applied to track Cr (VI) concentrations in laboratory samples, such as batch microcosms experiments with soil, surface water, and an anaerobic medium. The disclosed technology will prove useful to environmental practitioners, academic and research organizations, and industries for monitoring low concentrations of (multiple) relevant and common anions in environmental media, helping to decrease the sample requirement, time, and cost for analysis.

Ion chromatography is a method for separating ions based upon their interactions with a stationary phase, such as a resin, and the eluent (mobile phase). Ions will move through columns packed with a stationary phase at different speeds depending on their affinity for the stationary phase, and they will separate from each other based upon differences in ion charge and size. As the eluent passes through the column, ions with a weaker affinity for the resin will move through the column faster and be eluted first, while ions with a stronger affinity for the column will move through the column more slowly.

Upon exiting the column, the ions are measured by an electrical conductivity detector. This detector produces a chromatogram which plots conductivity vs. time. Each ion produces a peak on this graph, the area of which is dependent on the relative ion concentration in the injected solution. These measurements can then be used to determine concentrations of analytes in an unknown sample. To combat possible interference caused by the ions in the mobile phase, a suppressor may be used to remove the unwanted electrolyte prior to the conductivity measurement. As the solution passes through the suppressor, ions in the eluent are replaced with a nonionic species. Alternatively, if the eluent is sufficiently dilute or has a low conductivity, the use of a suppressor is not necessary.

Ion chromatography or devices for preforming such may comprise a sample loop, injector, column, including guard column and analytical column, suppressor, conductivity detector, data acquisition, storage, or processing device.

"Eluent" means the medium that transports the sample through the system and contributes to the selectivity of the separation. The eluent may comprise a solution of one or more salts in water that may act as a buffer, providing a stable pH. The ion strength, pH, temperature, flow rate, and buffer salt may individually, or collectively, influence the selectivity of the separation. The eluent may also comprise an organic modifier. The present technology utilizes an isocratic methodology. "Isocratic" means that the eluent has a constant concentration of buffer and/or organic modifier throughout the chromatographic process.

In some embodiments, the eluent comprises a carbonate. A carbonate eluent is an aqueous solution of carbonate and hydrogen carbonate salts. Such an eluent has the advantage that the total ionic strength as well as the proportions of monovalent ($HCO_3^-$) and divalent ($CO_3^{2-}$) ions can be varied and carbonic acid ($H_2CO_3$) may be formed as the eluent passes through the suppressor. In particular embodiments, the carbonate is provided as sodium carbonate. In some embodiments, the eluent comprises between 10.0 and 12.0 or 10.5 and 11.5 mM $Na_2CO_3$. In the Examples that follow, 10.8 mM $Na_2CO_3$ is used. In some embodiments, the eluent has a pH between 11.0 and 13.0 or 11.5 and 12.5. In the Examples, a pH of 11.9 was used.

In some embodiments, the eluent comprises an organic modifier. An "organic modifier" means an organic substance that may change in hydrophobic interactions between the analyte and the stationary phase; influence on ion solvation; and/or change in the Coulombic interactions between the analyte and the stationary phase. Suitably, the organic modifier may be included with eluent. In other embodiments, the organic modifier may be present in the column independent of the eluent. Exemplary organic modifiers include, but are not limited to, acetonitrile, acetone, and methanol. In some embodiments, the eluent comprises between 30% and 40% or 33% and 37% (v $v^{-1}$). In the examples 35% (v $v^{-1}$) of acetonitrile is used.

"Injector" means a device for the introduction of a sample volume into the column. In the load position, a sample loop can be filled with the sample solution and, optionally, the eluent may be bypassed to the column. When the injector is turned to the inject position, the eluent can pass through the sample loop and transfer the sample to the column. By varying the sample loop volume, the amount of sample introduced may be varied.

"Column" is a device for separating sample ions. The column may be packed with a stationary phase material comprising charged functional groups, or ion exchange groups, that allow for the sample ions to be separated. The column may be characterized by its capacity, selectivity, and efficiency. Capacity is determined by the column's ability to attract ions and the eluent strength required to elute these through the column. Selectivity is the column's ability to separate different analyst and is affected by the chemical and physical qualities of the column that results in interaction with the ions to be separated and the choice of eluent. Efficiency is the columns ability to produce well resolved or high and narrow chromatographic peaks. In some embodiments, the column is a polymer- or silica-based column where the stationary material comprises stationary material composed of a polymer or silica material, respectively.

The column may comprise a guard column and an analytical column. "Guard column" means a portion of the column that can scavenge debris or multivalent ions that would otherwise be accumulated within an analytical column. "Analytical column" means a portion of the column that effectively separates the analyte ions into resolvable chromatographic peaks. In some embodiments, the stationary phase of the analytical column comprises a polyvinyl alcohol with quaternary ammonium groups. The guard column may comprise the same stationary phase material as the analytical column but other stationary phase materials may also be used.

"Effective separation temperature" means a temperature where the ionic analytes are resolvable. Suitably, the effective separation temperature may be between 25.0-55.0° C., including any temperature or temperature range there between.

"Suppressor" means a device for lowering a background signal and increasing the useful signal. Because the eluent contains a relatively high amount of salt, the eluent contributes to background conductivity or signal. To differentiate between the background conductivity and signal from the analyte, the suppressor reduces the amount of dissolved ions in the eluent. The suppressor may provide a suppressor solution. The suppressor solution may comprise an acid, such as $H_2SO_4$.

"Detector" means a device for detecting, identifying, or quantifying the analyte ions. Suitably the detector is a conductivity detector. A conductivity detector detects the conductivity of the eluate that passes through a cell comprising a multiplicity (e.g., 2 or 4) of electrodes between which an electrical potential is applied. When the sample ions pass through the cell, the conductivity is increased. This increase in current is proportional to the increase in conductivity, which is a function of the ion concentration.

"Data acquisition, storage, or processing device" means device for acquiring, storing, or processing signal output from the detector. Suitably the data acquisition, storage, or processing device is a computer or other suitable device.

An isocratic IC method is disclosed with suppressed conductivity detection for simultaneous quantification of Cr (VI), $F^-$, $Cl^-$, $NO_2^-$, $NO_3^-$, $SO_4^{2-}$, Se (VI), As (V), and $ClO_4^-$. Most analytes showed good separation (defined as R>1.5). A typical chromatogram of the analytes (50 μg $L^{-1}$ each in DI water) is shown in FIG. 1. All the analytes showed good separation and were eluted within 20 min of sample injection (FIG. 1). Table 1 shows the resolution of peaks, linear regression equation, determination coefficient, LOD, and LOQ for the analytes. The determination coefficient of every analyte was >0.99 and the LOD was in the range of 0.1-7.5 μg $L^1$ (Table 1). These data demonstrate the capability of the method to quantify trace concentrations of the analytes. For Cr (VI), the LOD and LOQ were 0.2 μg $L^{-1}$ and 0.6 μg $L^{-1}$, respectively, which are three orders of magnitude lower than EPA's current MCL of 100 μg $L^{-1}$ Cr.

A comparison of published IC methods for measurement of Cr (VI) in aqueous samples is shown in Table 2. One of the advantages of the disclosed method over previously published IC methods for Cr (VI) quantification is that $ClO_4^-$ can also be quantified. The method was validated by demonstrating linearity, precision and accuracy for simultaneous quantification of all the anion analytes, which was not reported previously by other IC methods (Bruzzoniti et al., 1999; Kończyk et al., 2018). The LOD and LOQ for Cr (VI) was lowest among IC methods with suppressed conductivity detection. Low LOD and LOQ for Cr (VI) was achieved by using a 1000 µL injection loop, which is employed in the EPA Method for trace analysis of $ClO_4^-$ in drinking water (Hautman et al., 1999). Methods that use UV-Vis spectroscopy, chemiluminescence and thermal lens spectroscopy detection systems can achieve lower LOD for Cr (VI) but cannot quantify other anions.

Figure 2:
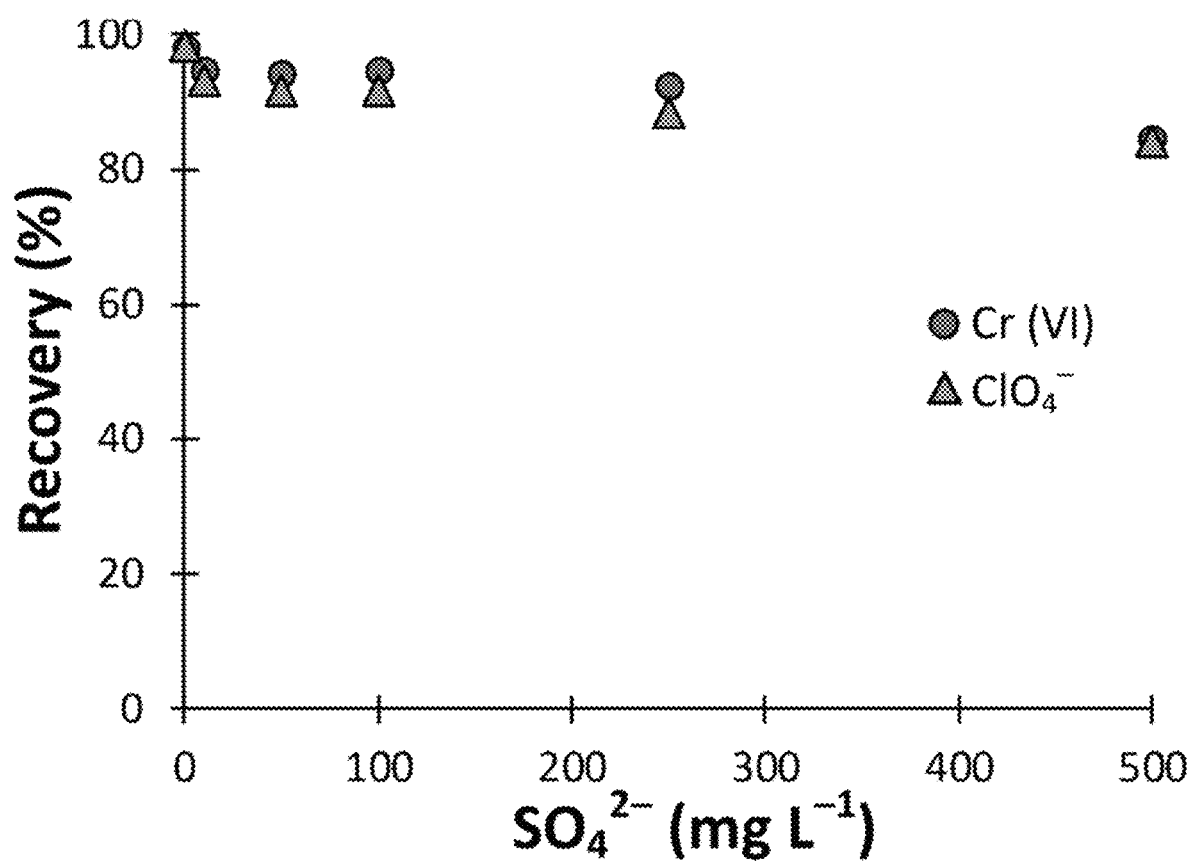
FIG. 2 shows the effect of $SO_4^{2-}$ concentration on recovery of Cr (VI) and $ClO_4^-$. The data are averages of triplicate measurements.

$SO_4^{2-}$ is among the most abundant anions in many environmental media. High $SO_4^{2-}$ concentrations can interfere with quantification of other analytes when conductivity detection is employed. In such cases, the sample needs to be diluted, making it challenging for trace analysis of the analytes using a conductivity detector. Alternatively, pre-treatment of the sample matrix to remove $SO_4^{2-}$ can be employed using pre-treatment cartridges, but these can severely affect the recovery of other analytes like Cr (VI). The effect of $SO_4^{2-}$ concentration up to 500 mg $L^{-1}$ on recovery of co-analytes was evaluated. $SO_4^{2-}$ concentration had no effect on recovery of $F^-$, $Cl^-$, $NO_2^-$ and $NO_3^-$ as these analytes eluted before $SO_4^{2-}$ in the disclosed method (FIG. 1). A recovery of 80% or greater is an acceptable criterion for quantification of chemical analytes. Se (VI) and As (V) recovery was <80% when $SO_4^{2-}$ concentration was ≥10 mg $L^{-1}$ (data not shown). However, Cr (VI) and $ClO_4^-$ recovery was ≥85% in the presence of up to 500 mg $L^{-1}$ $SO_4^{2-}$ (FIG. 2). These data demonstrate that the method can be used to quantify low concentrations of Cr (VI) and $ClO_4^-$ in matrices with a high concentration of $SO_4^{2-}$ without requiring pre-treatment or dilution of the sample.

The analytical accuracy (precision and trueness) was evaluated for quantification of the anions at three concentration levels (2 µg $L^{-1}$, 10 µg $L^{-1}$ and 100 µg $L^{-1}$) using the disclosed IC method. In reagent water or DI water, the US EPA's acceptance criterion for RSD is ≤10%. The acceptance criterion for recovery is 80-120% for mid-level check standards. The acceptance criterion for recovery is 50-150% at concentrations close to the LOD of the analyte (low-level check standard). Table 3 documents the recovery of all anion analytes. At 100 µg $L^{-1}$, all analytes were quantified with RSD<2.3% and the recovery was in the range of 96.2-107.9%, showing precision and trueness (accuracy) for quantification (Table 3). At 10 µg $L^{-1}$, the RSD and recovery for $F^-$ and $Cl^-$ were affected (RSD values >10% and recovery of 47.5-90.6% (Table 3)). These results are expected as 10 µg $L^{-1}$ is within a factor of three from the LOD of $F^-$ and $Cl^-$. All other analytes were quantified with RSD<7.4% and recovery of 92.6-105.3% using 10 µg $L^{-1}$ standard (Table 3). At 2 µg $L^{-1}$ concentration, all analytes except $NO_3^-$ were quantified with RSD<6% and recovery in the range of 95.8-106.4% (Table 3). Overall, the method accomplished accuracy in quantification of $NO_2^-$, Se (VI), As (V), $ClO_4^-$ and Cr (VI) at concentrations as low as 2 µg $L^{-1}$. At 100 µg $L^{-1}$, the RSD and recovery for all the analytes are well within the acceptance criteria. These data demonstrate accuracy for quantification of all the analytes.

To test the applicability of the disclosed IC method on environmental aqueous samples, the recovery of Cr (VI) was evaluated in contaminated surface water, groundwater, tap water, and wastewater samples (Table 4). The surface water sample was the only one with a detectable Cr (VI) concentration. The US EPA's acceptance criteria for recovery of analytes in environmental samples is 80-120%. As seen in Table 4, the Cr (VI) recovery ranged from 97.2±0.2% to 102.8±0.6%. The recovery of the other analytes was within the acceptable recovery criterion in most environmental samples (Table 4). These data support the applicability of this method for simultaneous quantification of the analytes in environmental aqueous samples.

The trueness of Cr (VI) concentration was evaluated in the surface water sample measured with the disclosed IC method by comparing it with the measured value using the EPA method 7196A (diphenylcarbazide based colorimetry method). The concentration of Cr (VI) in the surface water was 20.6±0.2 mg $L^{-1}$ using the diphenylcarbazide method (EPA Method 7196A). Assuming this was the true Cr (VI) concentration, the recovery of Cr (VI) concentration using the IC method was 100.2±3.4% (data not shown), demonstrating trueness for Cr (VI) quantification in the surface water sample. For Cr (VI) quantification using the IC method, the surface water was diluted 1000 times with reagent water to fit the Cr (VI) concentration within the calibration range.

Figure 3:
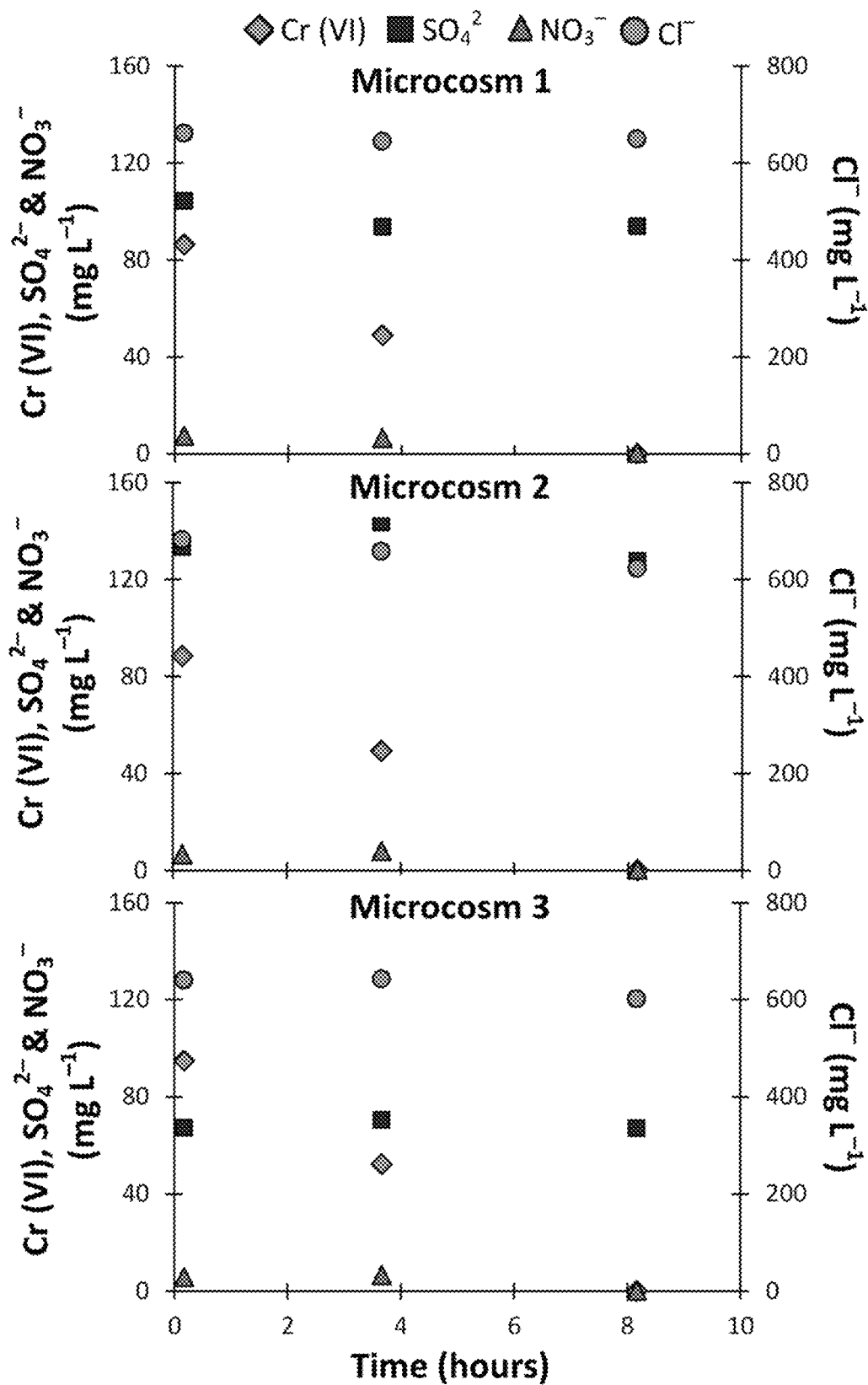
FIG. 3 shows the concentrations of Cr (VI), $SO_4^{2-}$, $NO_3^-$, and $Cl^-$ during incubation in replicate soil microcosms. Note that $Cl^-$ is plotted in the secondary y axis.

The IC analytical method was applied to simultaneously track concentrations of anions in typical batch microcosms used commonly used in laboratory settings. The microcosms in this study were focused on abiotic and microbiological Cr (VI) reduction. FIG. 3 shows the time course concentrations of Cr (VI) (naturally-present and spiked) and $SO_4^{2-}$, $NO_3^-$ and $Cl^-$ (naturally-present anions in the soil matrix). The concentration of Cr (VI) decreased from 90 mg $L^{-1}$ to below detection limit in eight hours, likely from abiotic reduction by reducing agents in the soil such as sulfide and iron bearing minerals and/or microbial reduction to Cr (III). The concentrations of $SO_4^{2-}$ and $Cl^-$ did not change significantly during the incubation time in the soil microcosms (FIG. 3). FIG. 4 tracks concentrations of Cr (VI) in culture-only microcosms focused on microbial reduction of Cr (VI) using a mixed culture. Cr (VI) concentration was reduced from ~15 mg $L^{-1}$ to <1 mg $L^{-1}$ in ~18 days. Data from FIGS. 3 and 4 highlight the applicability of the IC method in laboratory experiments using both complex environmental matrices containing multiple analytes and defined laboratory medium focused only on Cr (VI).

Due to the capability of quantifying several anions simultaneously, the IC method developed in this study is useful to environmental practitioners, academic and research organizations, and other industries that routinely measure Cr (VI) and co-occurring anions. An ion chromatograph equipped with a suppressed conductivity detector is a common instrumentation that many laboratories possess for quantification of common inorganic anions (e.g., $Cl^-$, $NO_3^-$, $SO_4^{2-}$) by EPA Method 9056A. Thus, the method developed can be adapted by laboratories that use the most common IC instrument. The Examples show that Cr (VI), As (V), Se (VI) and $ClO_4^-$ in the low µg $L^{-1}$ concentration range can be measured without pre-treatment of the sample or post column derivatization. The IC method from this work was shown to be reliable, precise, accurate, and suitable for monitoring important anions in environmental aqueous media, industrial wastewaters and laboratory experiments.

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Examples

Instrumentation

All analyses were performed using a Metrohm AG 930 compact IC flex system (Herisau, Switzerland). The IC was equipped with a chemical suppressor (Metrohm Suppressor Module (MSM)) and a conductivity detector. An 800 dosino regeneration system was used to deliver the chemical suppressor solution to the MSM. The Metrohm $CO_2$ Suppressor (MCS) removed the carbonate (as $CO_2$) produced during the chemical suppression reaction in the MSM. The anions were separated using a Metrosep A Supp 7 analytical column (250 mm×4 mm, Metrohm) and a Metrosep A Supp 5 Guard column (5 mm×4 mm, Metrohm). A Metrohm AG 919 IC autosampler plus was used for sample injection. The volume of the sample injection loop was 1000 μL. The data acquisition and processing were performed with the MagIC Net 3.2 Metrodata software.

Chemicals and Reagents

Reagent water, LC-MS Ultra CHROMASOLV® (Honeywell, Charlotte, NC), was used to prepare the standards and the sample dilutions. Cr (VI) standards were prepared using $K_2CrO_4$ (Sigma-Aldrich, St. Louis, MO). As (V) and Se (VI) standards were prepared using $Na_2HAsO_4 \cdot 7H_2O$ (J. T. Baker™, Phillipsburg, NJ) and $Na_2SeO_4$ (ACROS Organics™, Geel, Belgium). $ClO_4^-$ standards (Metrohm; Cat. #REAIC1023) and mixed anion standard (Metrohm; Cat. #REAIC1035) were used to generate the calibration curves for $ClO_4^-$, $F^-$, $Cl^-$, $NO_2^-$, $NO_3^-$, and $SO_4^{2+}$.

The eluent and the MSM suppressor solutions were prepared using deionized and purified water using a PURELAB® Ultra (ELGA LabWater, United Kingdom) with a specific resistance ≥18.2 M'Ω-cm. The eluent (mobile phase) contained 10.8 mM $Na_2CO_3$ (3% (v $v^{-1}$) of Metrohm's A Supp 7 eluent 100× concentrate) and 35% (v $v^{-1}$) gradient grade acetonitrile (Sigma-Aldrich) in deionized water. The pH of the eluent was 11.9±0.02. The MSM suppressor solution contained 500 mM $H_2SO_4$ in deionized water.

The 10% (v $v^{-1}$) $H_2SO_4$ and 10% (v $v^{-1}$) $H_3PO_4$ solutions for colorimetric determination of Cr (VI) were prepared from concentrated $H_2SO_4$ (95-98% solution; VWR™, Randor, PA) and concentrated $H_3PO_4$ (85% solution; Alfa Aesar™, Haverhill, MA), respectively. The complexing reagent contained 5 g $L^{-1}$ of 1,5-diphenylcarbazide (Sigma-Aldrich) in acetone.

Analytical Methods

The IC method used a constant eluent flow rate of 0.8 mL $min^{-1}$ and a constant column/oven temperature of 55° C. The MSM stepping interval was 10 mins and the conductivity detector was set at 2.3% per ° C. At these conditions, the back pressure was 12±0.4 MPa. The pump start-up time was at 45 to 60 min during the equilibration of the instrument. Calibrations for the anion analytes were established by injecting quadruplicates of 1, 5, 10, 25, 50, 100 and 200 μg $L^{-1}$ standard mixture. The calibration range for $NO_3^-$, Se (VI), As (V), $ClO_4^-$, and Cr (VI) was 1-200 μg $L^{-1}$. For $Cl^-$, $NO_2^-$ and $SO_4^{2-}$, the calibration range was 5-200 μg $L^{-1}$. $F^-$ was calibrated in the range of 10-200 μg $L^{-1}$.

EPA Method 7196A was used to quantify Cr (VI) in a contaminated surface water sample and compare the concentrations obtained by the IC method. Cr (VI) concentration was determined colorimetrically at 540 nm using the diphenylcarbazide method (US EPA, 1992). Briefly, 0.1 mL of sample or standard was added to a 10 mL test tube followed by addition of 1 mL each of 10% $H_2SO_4$ and 10% $H_3PO_4$. Then, 0.1 mL diphenylcarbazide solution (5 g $L^{-1}$ DPC in acetone) was added to a test tube. The mixture was then vortexed and incubated at room temperature for 5 min. Absorbance of the magenta color was analyzed using a Varian Cary 50 UV-Vis spectrophotometer (Agilent, Santa Clare, CA) at 540 nm. The spectrophotometer was calibrated using the standard Cr (VI) solution. The calibration range for the colorimetry method was 0.5-75 mg $L^1$ Cr (VI) and the detection limit was 0.25 mg $L^{-1}$.

Environmental Samples

Tap water from the city of Tempe and reverse osmosis (RO) grade water (US Water Systems™, Indianapolis, IN) were collected at the Biodesign Institute, Arizona State University, Tempe, AZ. Tap water from the City of Mesa was collected from a domicile in Mesa, AZ. Three groundwater samples were obtained for testing. One groundwater sample was from the Phoenix Goodyear Airport-North Superfund site, Arizona, USA. The other samples were collected from two confidential sites in the Southwestern United States. Cr (VI) contaminated surface water was collected from Tamilnadu Chromates and Chemicals Ltd. (TCCL), an abandoned chromate manufacturing facility in Ranipet, Tamil Nadu, India. The wastewater samples used in this study were received from a power station in the Eastern United States and from the Northwest Water Reclamation Plant, Mesa, AZ, USA.

Laboratory Microcosm Experiments

The developed IC method was applied to monitor anions in soil and culture-only batch microcosms. Soil laboratory microcosms focused on abiotic and microbiological Cr (VI) reduction were established in 160 mL glass serum bottles with 25 g of Cr (VI)-contaminated soil and 100 mL anaerobic mineral medium as described elsewhere. The soil was collected from 0-0.25 m depth at the TCCL site, India, and was homogenized in the anaerobic glove chamber (Coy Laboratory Products Inc., Grass Lake, MI) under 3.5% $H_2$ and 96.5% $N_2$ atmosphere. 2 g $L^{-1}$ yeast extract and 10 mM lactate were added to the microcosms as electron donor and carbon sources for microorganisms. The initial Cr (VI) concentration in the soil microcosms was ~ 90 mg $L^{-1}$.

Culture-only microcosms focused on microbiological Cr (VI) reduction were established in 160 mL serum bottles containing 100 mL anaerobic mineral medium as used in soil microcosms. The inoculum (4% v $v^{-1}$ inoculum) was a mixed culture grown on Cr (VI) and lactate. The culture-only microcosms were amended with 1 g $L^{-1}$ yeast extract and 3 mM lactate. The initial concentration of Cr (VI) was 15 mg $L^{-1}$. All (soil and culture-only) microcosms were established in triplicates, were incubated in the dark at 30° C., and were shaken on a platform shaker at 125 RPM. Liquid samples from the microcosms were sampled at various time points during incubation. The liquid samples were filtered using 0.2 μm syringe filters (mdi Membrane Technologies Inc., Harrisburg, PA) and analyzed for anions using the disclosed IC method.

Tables

TABLE 1

Resolution, regression equation, determination coefficient, quantification range, LOQ, and LOD of 9 analytes using the method from this study. R values greater than 1.5 are baseline resolutions. Y = peak area ((μS $cm^{-1}$) × min); X = concentration (μg $L^{-1}$). NA = Not applicable (Cr (VI) was the last analyte in the method run).

| Elution order | Analyte | Resolution (R) | Regression equation | $R^2$ | Quantification range (μg $L^{-1}$) | LOD (μg $L^{-1}$) | LOQ (μg $L^{-1}$) |
|---|---|---|---|---|---|---|---|
| 1 | $F^-$ | 3.05 | Y = 0.0071X + 0.1517 | 0.9986 | 24.9-1000 | 7.5 | 24.9 |
| 2 | $Cl^-$ | 1.03 | Y = 0.0083X + 0.0541 | 0.9984 | 14.4-10000 | 4.3 | 14.4 |
| 3 | $NO_2^-$ | 2.92 | Y = 0.002X + 0.0082 | 0.9979 | 1.5-5000 | 0.4 | 1.5 |
| 4 | $NO_3^-$ | 5.51 | Y = 0.0122X + 0.0009 | 0.9981 | 1.9-10000 | 0.6 | 1.9 |
| 5 | $SO_4^{2-}$ | 2.45 | Y = 0.0067X + 0.0903 | 0.9983 | 9.5-10000 | 2.9 | 9.5 |
| 6 | Se (VI) | 1.55 | Y = 0.0066X + 0.0024 | 0.9999 | 0.5-9000 | 0.2 | 0.5 |
| 7 | As (V) | 2.51 | Y = 0.0023X − 0.009 | 0.9988 | 2.1-7000 | 0.6 | 2.1 |
| 8 | $ClO_4^-$ | 3.71 | Y = 0.0025X − 0.0045 | 0.9992 | 0.5-10000 | 0.1 | 0.5 |
| 9 | Cr (VI) | NA | Y = 0.0041X + 0.0046 | 0.9998 | 0.6-10000 | 0.2 | 0.6 |

TABLE 2

Comparison of various IC methods for Cr (VI) quantification in aqueous samples. NR = not reported.

| Detection system | Post-column derivatization | LOD (μg $L^{-1}$) | LOQ (μg $L^{-1}$) | Sample injection volume (μL) | Simultaneous detection of other anions | Reference |
|---|---|---|---|---|---|---|
| UV-Vis spectroscopy | Yes | [a]0.01 | [a]0.036 | [a]1250 | No | U.S. EPA method 218.7 (Zaffiro et al., 2011) |
| Chemiluminescence detection | Yes | 0.09 | NR | 50 | No | (Gammelgaard et al., 1997) |
| Thermal lens spectrometry | Yes | 0.1 | NR | 200 | No | [b](Šikovec et al., 2001) |
| Direct UV detection | No | 0.2 | 1.2 | 100 | No | (Michalski, 2003) |
| Suppressed conductivity | No | 13.5 | 44.7 | 10 | Cyanide, thiocyanate, cyanate | (Destanoğlu and Gümüş Yilmaz, 2016) |
| Suppressed conductivity | No | 2 | NR | 200 | $Cl^-$, $NO_3^-$, $SO_4^{2-}$, Se (IV), Se (VI), W (VI), As (V), Mo (VI) | [b](Bruzzoniti et al., 1999) |
| Suppressed conductivity | No | NR | NR | 100 | $F^-$, $Cl^-$, $Br^-$, $NO_3^-$, $PO_4^{3-}$, $SO_4^{2-}$ | [b](Kończyk et al., 2018) |

TABLE 2-continued

Comparison of various IC methods for Cr (VI) quantification in aqueous samples. NR = not reported.

| Detection system | Post-column derivatization | LOD ($\mu g\ L^{-1}$) | LOQ ($\mu g\ L^{-1}$) | Sample injection volume ($\mu L$) | Simultaneous detection of other anions | Reference |
|---|---|---|---|---|---|---|
| Suppressed conductivity | No | 0.2 | 0.6 | 1000 | $F^-$, $Cl^-$, $NO_2^-$, $NO_3^-$, $SO_4^{2-}$, Se (VI), As (V), $ClO_4^-$ | This study |

[a]Values from carbonate/bicarbonate eluent system.
[b]Linear regression equation, precision, and trueness were not reported.

TABLE 3

Analyte accuracy of quantification using the method from this study. NA = not applicable (concentration below LOD).

| Elution order | Analyte | Spiked concentration 2 $\mu g\ L^{-1}$ (n = 6) | | Spiked concentration 10 $\mu g\ L^{-1}$ (n = 6) | | Spiked concentration 100 $\mu g\ L^{-1}$ (n = 6) | |
|---|---|---|---|---|---|---|---|
| | | Precision (RSD (%)) | Trueness (recovery (%)) | Precision (RSD (%)) | Trueness (recovery (%)) | Precision (RSD (%)) | Trueness (recovery (%)) |
| 1 | $F^-$ | NA | NA | 20.3 | 47.5 | 2.2 | 99.5 |
| 2 | $Cl^-$ | NA | NA | 12.2 | 90.6 | 0.9 | 96.2 |
| 3 | $NO_2^-$ | 0.0 | 95.8 | 2.4 | 97.2 | 1.3 | 97.6 |
| 4 | $NO_3^-$ | 60.7 | 42.6 | 3.1 | 99.1 | 0.9 | 96.3 |
| 5 | $SO_4^{2-}$ | NA | NA | 7.3 | 92.6 | 1.5 | 101.0 |
| 6 | Se (VI) | 3.2 | 106.4 | 1.3 | 100.8 | 0.8 | 102.2 |
| 7 | As (V) | 0.0 | 102.2 | 0.0 | 101.7 | 0.7 | 107.9 |
| 8 | $ClO_4^-$ | 0.0 | 104.6 | 1.6 | 105.3 | 0.7 | 103.1 |
| 9 | Cr (VI) | 5.2 | 98.3 | 1.7 | 100.1 | 0.7 | 98.7 |

TABLE 4

Recovery of all anion analytes in environmental samples. The data are averages with standard deviation of triplicates. The spiking concentration for all anions was 100 $\mu g\ L^{-1}$. ND = Not determined.

| Samples | Cr (VI) recovery (%) | $F^-$ recovery (%) | $Cl^-$ recovery (%) | $NO_2^-$ recovery (%) | $NO_3^-$ recovery (%) | $SO_4^{2-}$ recovery (%) | Se (VI) recovery (%) | As (V) recovery (%) | $ClO_4^-$ recovery (%) |
|---|---|---|---|---|---|---|---|---|---|
| DI water | 100.9 ± 0.5 | 94.5 ± 1.2 | 93.5 ± 0.8 | 98.1 ± 1.3 | 96.5 ± 0.6 | 102.1 ± 1.5 | 104.3 ± 0.9 | 103.2 ± 0.7 | 103.3 ± 0.6 |
| RO water (Tempe, AZ) | 100.1 ± 0.3 | ND | ND | ND | ND | ND | ND | ND | ND |
| Tap water (Tempe, AZ) | 102.1 ± 0.3 | ND | ND | ND | ND | ND | ND | ND | ND |
| Tap water (Mesa, AZ) | 100.5 ± 0.6 | ND | ND | ND | ND | ND | ND | ND | ND |
| Groundwater (Goodyear, AZ) | 97.6 ± 0.3 | ND | ND | ND | ND | ND | ND | ND | ND |
| Groundwater (confidential site 1) | 100.2 ± 0.0 | 107.8 ± 7.0 | 101.5 ± 3.0 | 92.7 ± 2.3 | 109.2 ± 6.1 | 104.2 ± 2.8 | 94.3 ± 2.6 | 84.9 ± 4.9 | 95.9 ± 0.5 |
| Groundwater (confidential site 2) | 99.7 ± 0.6 | 82.6 ± 3.6 | 100.3 ± 2.5 | 85.0 ± 0.7 | 109.7 ± 1.9 | 111.8 ± 3.1 | 89.1 ± 0.2 | 71.0 ± 4.9 | 93.2 ± 0.4 |
| Surface water (Tamilnadu, India) | 102.8 ± 0.6 | 86.1 ± 4.6 | 95.5 ± 0.4 | 92.5 ± 2.1 | 90.7 ± 2.7 | 89.5 ± 1.4 | 108.8 ± 0.2 | 98.7 ± 7.2 | 92.3 ± 0.6 |
| Wastewater (confidential site 3, Eastern United States) | 99.5 ± 0.3 | ND | ND | ND | ND | ND | ND | ND | ND |
| Wastewater (Water Reclamation Plant, Mesa, AZ) | 97.2 ± 0.2 | 107.8 ± 3.7 | 108.8 ± 5.2 | 76.1 ± 2.4 | 103.7 ± 2.9 | 84.2 ± 0.3 | 97.0 ± 0.8 | 97.0 ± 0.5 | 101.2 ± 0.4 |

REFERENCES

Bruzzoniti, M. C., Mentasti, E., Sarzanini, C., 1999. Simultaneous determination of inorganic anions and metal ions by suppressed ion chromatography. Analytica chimica acta 382, 291-299.

California Water boards, 2018. Hexavalent Chromium in Drinking Water

Destanoğlu, O., Gümüş Yilmaz, G., 2016. Determination of cyanide, thiocyanate, cyanate, hexavalent chromium, and metal cyanide complexes in various mixtures by ion chromatography with conductivity detection. Journal of Liquid Chromatography & Related Technologies 39, 465-474.

Gammelgaard, B., Liao, Y.-p., Jøns, O., 1997. Improvement on simultaneous determination of chromium species in aqueous solution by ion chromatography and chemiluminescence detection. Analytica chimica acta 354, 107-113.

Hautman, D. P., Munch, D. J., Eaton Andrew, D., Haghani Ali, W., 1999. EPA Method 314.0: Determination of perchlorate in drinking water using ion chromatography.

Kończyk, J., Muntean, E., Michalski, R., 2018. Simultaneous determination of chromate and common inorganic anions using suppressed ion chromatography. Chemistry, Environment, Biotechnology 21, 11-13.

Michalski, R., 2003. Ion chromatography method for the determination of trace levels of chromium (VI) in water. Polish Journal of Environmental Studies 13, 73-78.

Šikovec, M., Franko, M., Novič, M., Veber, M., 2001. Effect of organic solvents in the on-line thermal lens spectrometric detection of chromium (III) and chromium (VI) after ion chromatographic separation. Journal of Chromatography A 920, 119-125.

US EPA, 1992. Method 7196A: Chromium, Hexavalent (Colorimetric).

US EPA, 2007. Method 9056A: Determination of inorganic anions by ion chromatography.

US EPA, 2010. Chromium in Drinking Water.

World Health Organization, 2003. Guidelines for Drinking-water Quality|Chromium.

Zaffiro, A., Zimmerman, M., Wendelken, S., Smith, G., Munch, D., 2011. METHOD 218.7: Determination of hexavalent chromium in drinking water by ion chromatography with post-column derivatization and UV-Visible spectroscopic detection.

We claim:

1. A method for simultaneous quantification of anions, the method comprising:
   loading a sample loop with an aqueous sample;
   injecting the sample from the sample loop into a column with an eluent, wherein the column comprises a guard column and an analytical column;
   separating, with the column, the injected sample at an effective separation temperature in the presence of an organic modifier into a multiplicity of detectable ionic analytes comprising Cr(VI), Se(VI), As(V), and $ClO_4^-$;
   suppressing, with a suppressor, a background signal; and
   simultaneously quantifying, with a conductivity detector, the multiplicity of ionic analytes.

2. The method of claim 1, wherein the multiplicity of detectable ionic analytes comprises $CrO_4^{2-}$, $AsO_4^{3-}$, $SeO_4^{2-}$, $ClO_4^-$, $F^-$, $Cl^-$, $NO_2^-$, $NO_3^-$, and $SO_4^{2-}$ and the detectable ionic analytes are simultaneously detected.

3. The method of claim 1, wherein the organic modifier is acetonitrile.

4. The method of claim 1, wherein the effective separation temperature is between 25.0-55.0° C.

5. The method of claim 1, wherein the eluent comprises carbonate.

6. The method of claim 1, wherein the analytical column comprises a polyvinyl alcohol with quaternary ammonium groups.

7. The method of claim 1, wherein the suppressor comprises a chemical suppressor and a $CO_2$ suppressor.

8. The method of claim 1, wherein the eluent comprises carbonate, the organic modifier is acetonitrile, the analytical column comprises a polyvinyl alcohol with quaternary ammonium groups, and $CrO_4^{2-}$, $AsO_4^{3-}$, $SeO_4^{2-}$, $ClO_4^-$, $F^-$, $Cl^-$, $NO_2^-$, $NO_3^-$, and $SO_4^{2-}$ are simultaneously detected.

9. The method of claim 8, wherein the limit of detection (LOD) of $CrO_4^{2-}$ is less than 2.0 µg $L^{-1}$.

10. A system for simultaneous quantification of anions, the system comprising:
    an eluent;
    an organic modifier;
    an injector;
    a column, the column comprising a guard column and an analytical column;
    a suppressor; and
    a conductivity detector,
    wherein the injector is configured to inject an aqueous sample from a sample loop into the column with the eluent, the column is configured to separate the injected sample in the presence of the organic modifier into a multiplicity of detectable ionic analytes comprising Cr (VI), Se(VI), As(V), and $ClO_4^-$ at an effective separation temperature, the suppressor is configure to suppress a background signal, and the detector is configured for simultaneous quantification of the multiplicity of ionic analytes.

11. The system of claim 10, wherein the system is configured for simultaneous detection of $CrO_4^{2-}$, $AsO_4^{3-}$, $SeO_4^{2-}$, $ClO_4^-$, $F^-$, $Cl^-$, $NO_2^-$, $NO_3^-$, and $SO_4^{2-}$.

12. The system of claim 10, wherein the organic modifier is acetonitrile.

13. The system of claim 10, wherein the system is configured to provide an effective separation temperature between 25.0-55.0° C.

14. The system of claim 10, wherein the eluent comprises carbonate.

15. The system of claim 10, wherein the analytical column comprises a polyvinyl alcohol with quaternary ammonium groups.

16. The system of claim 10, wherein the suppressor comprises a chemical suppressor and a $CO_2$ suppressor.

17. The system of claim 10, wherein the eluent comprises carbonate, the organic modifier is acetonitrile, the analytical column comprises a polyvinyl alcohol with quaternary ammonium groups, and the system is configured for simultaneous detection of $CrO_4^{2-}$, $AsO_4^{3-}$, $SeO_4^{2-}$, $ClO_4^-$, $F^-$, $Cl^-$, $NO_2^-$, $NO_3^-$, and $SO_4^{2-}$.

18. The system of claim 17, wherein the limit of detection (LOD) of $CrO_4^{2-}$ is less than 2.0 µg $L^{-1}$.

* * * * *